Figure 1:
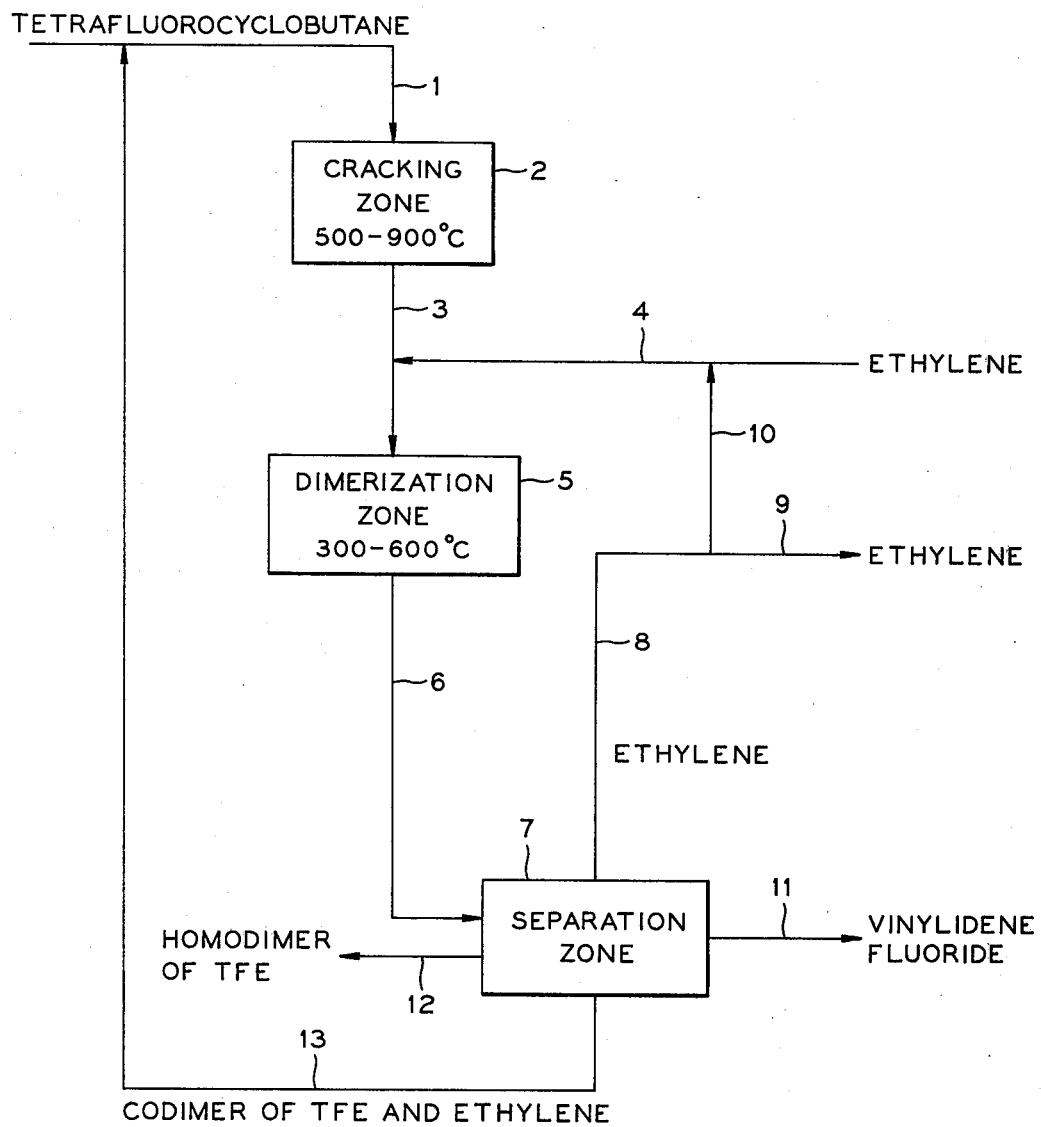

United States Patent [19]

Fozzard

[11] 3,996,301
[45] Dec. 7, 1976

[54] PRODUCING VINYLIDENE FLUORIDE SUBSTANTIALLY FREE FROM TETRAFLUOROETHYLENE

[75] Inventor: George B. Fozzard, Bartlesville, Okla.

[73] Assignee: Phillips Petroleum Company, Bartlesville, Okla.

[22] Filed: Sept. 22, 1972

[21] Appl. No.: 291,353

[52] U.S. Cl. ............................................ 260/653.3
[51] Int. Cl.² ........................................ C07C 21/02
[58] Field of Search ................ 260/653.3, 653.1 R, 260/658

[56] References Cited
UNITED STATES PATENTS

| | | | |
|---|---|---|---|
| 2,462,345 | 2/1949 | Barrick | 260/648 F |
| 2,733,278 | 1/1956 | Anderson | 260/653.3 |

Primary Examiner—James O. Thomas, Jr.
Assistant Examiner—James H. Reamer

[57] ABSTRACT

Tetrafluorocyclobutane is cracked to produce vinylidene fluoride and unavoidably minor amounts of tetrafluoroethylene and ethylene. The reaction effluent to which additional ethylene can be added is subjected to dimerization and/or codimerization conditions under which tetrafluoroethylene is converted to a product or products which can be removed from the desired vinylidene fluoride by conventional fractionation without danger of explosion. Separated tetrafluorocyclobutane can be recycled to the cracking operation. Octafluorocyclobutane can be cracked under optimum conditions in separate zone, usually more severe than those employed for tetrafluorocyclobutane.

8 Claims, 1 Drawing Figure

*VINYLIDENE FLUORIDE PROCESS*

VINYLIDENE FLUORIDE PROCESS

PRODUCING VINYLIDENE FLUORIDE SUBSTANTIALLY FREE FROM TETRAFLUOROETHYLENE

This invention relates to the production of vinylidene fluoride. It also relates to the removal of tetrafluoroethylene (TFE) from vinylidene fluoride. Further, it relates to a combination process for producing vinylidene fluoride substantially freed from tetrafluoroethylene.

In one of its concepts, the invention provides a method for removing in the vapor phase tetrafluoroethylene from a cracked effluent containing it and vinylidene fluoride, for example, as obtained by cracking tetrafluorocyclobutane (TFCB). In another of its concepts, the invention provides a combination process wherein tetrafluorocyclobutane is cracked at an elevated temperature, a cracked effluent thus obtained is subjected in a now preferred embodiment in the presence of added ethylene to dimerization conditions to homodimerize tetrafluoroethylene or to codimerize the same with ethylene whereupon the homodimer and codimer are separated permitting the recovery of vinylidene fluoride substantially freed from tetrafluoroethylene. In a further concept of the invention, ethylene is combined with the cracking zone effluent and passed together therewith into the dimerization zone.

I have conceived a combination of steps which permits the removal of tetrafluoroethylene from desirable vinylidene fluoride as produced by cracking tetrafluorocyclobutane at an elevated temperature. In this combination of steps, the cracked effluent containing tetrafluoroethylene, vinylidene fluoride and ethylene are subjected to conditions of dimerization preferably in the presence of added ethylene yielding a dimerization zone effluent containing homodimer of tetrafluoroethylene and/or codimer of tetrafluoroethylene with ethylene from which the vinylidene fluoride can be readily separated by fractionation. The homodimer of TFE (octafluorocyclobutane) produced in the dimerization zone can be removed from the process and transferred to a separate zone for cracking to two molecules of tetrafluoroethylene. The codimer of tetrafluoroethylene and ethylene, tetrafluorocyclobutane, can be recycled to the cracking zone for production of additional vinylidene fluoride.

An object of this invention is to produce vinylidene fluoride. Another object of this invention is to produce vinylidene fluoride substantially freed from tetrafluoroethylene. A still further object of the invention is to provide a process for producing vinylidene fluoride substantially freed from tetrafluoroethylene by cracking tetrafluorocyclobutane. A still further object of the invention is to provide a combination operation in which TFE is converted so that a resultant mixture can be separated as by fractionation, or other suitable means, to recover essentially pure vinylidene fluoride.

Other aspects, objects, and several advantages of this invention are apparent from a study of this disclosure, the drawing and the appended claims.

According to the present invention there is provided a process for the production of vinylidene fluoride which comprises the steps of cracking under cracking conditions in a cracking zone tetrafluorocyclobutane (TFCB), passing the cracked effluent, with some cooling to a dimerization zone, maintaining the cracked effluent in said zone, preferably with presence of ethylene therein, under dimerization and/or codimerization conditions until a substantial desired conversion of tetrafluoroethylene has taken place, then subjecting the dimerized materials to fractionation or other separation to recover vinylidene fluoride substantially freed from tetrafluoroethylene and other products at least some of which can be recycled to the cracking zone. The ethylene in the dimerization zone now is preferably added to said zone directly.

The present invention provides a method for conveniently removing TFE from reaction mixtures as herein described without resorting to fractionation procedures which could involve the handling of concentrated liquid TFE. The process removes TFE from the reaction mixture so that it can be recycled and re-used to produce more vinylidene fluoride. Thus, a TFE-containing reaction mixture is subjected to conditions of temperature and time which will selectively homodimerize or codimerize TFE, as with ethylene, with little or no effect on the vinylidene fluoride major product. The codimer of TFE and ethylene, thus obtained, can be recycled to the cracking zone. The homodimer can be cracked to TFE in a separate zone.

A method for producing vinylidene fluoride ($CF_2=CH_2$) by the thermal cracking of tetrafluorocyclobutane (TFCB) which is readily available by the codimerization of tetrafluoroethylene (TFE) and ethylene is known. See U.S. Pat. No. 2,733,278, issued Jan. 1, 1936, and U.S. Pat. No. 2,462,345, issued Feb. 22, 1949. Even though the cracking of the TFCB is relatively efficient and selective, minor amounts of TFE are formed in the cracking zone. TFE is known to be explosively polymerizable in liquid phase but not in the diluted vapor phase. However, a problem arises when the reaction mixture, which can contain about 0.1–5 wt. % TFE, is sought to be subjected to conventional purification operations which involve the concentration, separation, and liquefaction of the TFE. In the undiluted liquid form, TFE must be handled very carefully. A complicating factor is that the boiling points of TFE and vinylidene fluoride are relatively close.

TFCB is cracked to vinylidene fluoride using any process, apparatus, and conditions which are suitable for producing high yields of the desired vinylidene fluoride. Generally, this can be carried out thermally at temperatures of 500° – 900° C. The pressure in the cracking zone is not critical but should be as low as conveniently operable. Frequently, pressures less than about 50 psig are utilized. If desired, inert diluents such as helium, nitrogen, carbon tetrafluoride, and the like, can be present in the reaction zone which can contain considerable ethylene as well.

The residence time in the cracking zone will depend upon the cracking temperature, low temperatures requiring longer residence time, and vice versa. Broadly, residence times ranging from about 1 second up to about 10 minutes can be used. Complete conversions or even high cracking conversions are not a necessity because TFCB is a comparatively high boiling material which can be easily separated from the relatively low boiling, cracked products in the cracking effluent and recycled to the cracking zone. Thus, cracking conversions of 20 – 60 percent are generally convenient.

According to the invention, the entire effluent from the cracking zone can be passed into a dimerization zone. Or the effluent can be treated as desired to separate and remove one or more components from the effluent stream. For example, some or all of the relatively high boiling TFCB can be removed, if desired, but this is not at all necessary. The dimerization zone is operated under conditions which are severe enough to cause the dimerization of TFE, or the codimerization of TFE with ethylene, at a substantial rate yet mild enough to minimize or prevent decomposition of the vinylidene fluoride major product. This is accomplished according to the invention by a suitable combination of conditions which include temperature, pressure, and residence time in the dimerization zone. The dimerization can be carried out in any apparatus which is suitable for high temperatures and high pressure operation. Carbon steel is presently preferred to stainless steel as a material of construction for such a dimerization reaction.

The dimerization temperature will generally be in the approximate range 300° − 600° C, preferably about 400° − 600° C, with the lower temperatures requiring longer residence times and vice versa. Pressure favors the dimerization reaction and, accordingly, the pressure within the dimerization zone should be as high as can be conveniently practical. Dimerization pressures will generally be in the range of 0 − 10,000 psig, and more often in the range of about 50 − 500 psig as a compromise between dimerization efficiency and cost of apparatus.

The residence time in the dimerization zone will depend upon the dimerization temperature. Broadly, the residence time can range from 0.1 minute to 200 hours. Generally, continuous operations will employ the highest temperatures when residence times can range from 0.1 minute to 20 minutes. In batch reactions, somewhat lower temperatures can be used and residence times of 1 − 200 hours can be used. The conditions desired by one skilled in the art having studied this disclosure can be determined by mere routine testing.

Generally, at least a minor amount of ethylene will be present in the cracked mixture subjected to the conditions of the dimerization zone. If desired, however, additional ethylene can be introduced into the dimerization zone for the purpose of facilitating the formation of the codimer with TFE. This has several advantages. The codimer of ethylene and TFE is TFCB which is readily separable and directly recyclable to the cracking zone. The homodimer of TFE, OFCB, is also readily separable. It can be removed from the process and transferred to a separate cracking zone where it is cleaved to two molecules of TFE. Consequently, it is desirable to introduce additional ethylene into the dimerization zone, particularly if there is insufficient ethylene in the cracker effluent. This will aid to prevent a build-up of TFE in the system.

The amount of additional ethylene which can be introduced into the dimerization zone is limited only by the available means by which it can be conveniently recovered in later separation stages and recycled. The greater the ratio of ethylene to TFE, the more rapid the codimerization of TFE. Consequently, the molar ratio of ethylene to TFE maintained in the dimerization zone can be in the broad range of 1:1 to about 100:1, preferably 1:1 to about 10:1.

In the separation stage of the process, any convenient means or combination of means which is suitable for separating the mixture into a high purity vinylidene fluoride stream, OFCB, TFCB, and ethylene can be used. The TFCB can be recycled to the cracking zone; the ethylene can be recycled to the dimer zone; and the OFCB can be cracked to TFE in a separate zone. Since most, if not all, of the TFE will be converted in the dimerization zone, the dimerization effluent can be subjected to conventional fractionation for the desired separations.

The table below shows the boiling points at atmospheric pressure of the principal materials involved in the invention process:

| | |
|---|---|
| Tetrafluorocyclobutane (TFCB) | 50° C |
| Octafluorocyclobutane (OFCB) | −6° C |
| Tetrafluoroethylene (TFE) | −82° C |
| Vinylidene Fluoride | −104° C |
| Ethylene | −76° C |

It is readily seen from the table that the present invention can avoid the difficult separation of the relatively closely boiling vinylidene fluoride and TFE. On the other hand, converting the TFE to the homodimer (OFCB) or the codimer (TFCB) provides much more readily separable mixtures.

Referring now to the drawing, tetrafluorocyclobutane passes by 1 into cracking zone 2 wherein it is cracked under conditions described herein. Cracking zone effluent 3 is passed preferably with additional ethylene introduced at 4 into dimerization zone 5. In the dimerization zone, the tetrafluoroethylene is substantially converted as herein described. The effluent from the dimerization zone is passed by 6 into separation zone 7 from which ethylene is recovered at 8 and can be removed from the process at 9 or reused as already described by way of crossover 10. Vinylidene fluoride substantially freed from tetrafluoroethylene is removed at 11. Codimer of tetrafluoroethylene and ethylene is recycled by 13 and 1 to cracking zone 2. Homodimer of tetrafluoroethylene removed through 12 can be subjected to cracking in a separate zone (not shown) as described herein.

EXAMPLE I

A stream of gaseous helium, at a rate of about 50 cc/minute, was saturated at room temperature with TFCB and then passed into a cracking zone. The cracking zone consisted of a ¾ inch ID carbon steel pipe, packed with steel wool, which was about 10 inches long. It was externally heated to maintain an inside temperature of about 600° C. The feed was passed into the zone at atmospheric pressure. The conversion of TFCB in the cracking zone was about 20 percent.

The cracking zone effluent was passed into an ice water-cooled trap to separate some of the unconverted TFCB, but relatively little was removed. The effluent was then passed into a dimerization zone. This zone consisted of a 150 cc stainless steel bomb which was externally heated to maintain an elevated temperature. The pressure within this zone was also atmospheric.

Tests were carried out at 458° C and at 500° C. At each of these temperatures, the feedstream entering the dimerization zone and the effluent leaving the dimerization zone was sampled and analyzed by gas-liquid chromotography. The results of these analyses, in area percent, are shown in Table I below. In all the analyses, the high boiling TFCB and OFCB contents of the streams were neglected for convenience.

Table I

| Ethylene | TFE | $CF_2=CH_2$ |
|---|---|---|
| At 458° C | | |

Table I-continued

|  | Ethylene | TFE | CF$_2$=CH$_2$ |
|---|---|---|---|
| Dimerization Feed | 4.85 | 2.68 | 92.47 |
| Dimerization Effluent | 4.11 | 2.33 | 93.56 |
| At 500° C |  |  |  |
| Dimerization Feed | 4.28 | 2.74 | 92.98 |
| Dimerization Effluent | 2.69 | 2.03 | 95.29 |

The data in the table above show that at temperatures of 458° C and at 500° C the TFE content of the cracking zone effluent is significantly reduced by passing through the dimerization zone. This can be accomplished with no significant loss of the vinylidene fluoride major product in the sense at least that a good purity product is obtained. These results indicated that still greater reduction of TFE could be accomplished under more severe dimerization conditions of temperature, residence time, and pressure.

EXAMPLE II

To test the effects of still more severe dimerization zone conditions, a synthetic mixture of vinylidene fluoride, ethylene, and TFE was prepared and subjected to dimerization conditions in a batch reaction.

A 200 ml stainess steel cylinder which was used as a reactor was evacuated then filled to 0 psig with vinylidene fluoride. Sufficient TFE was then added to this cylinder to increase the pressure to 5 psig; following this ethylene was added to increase the pressure to 10 psig; and finally vinylidene fluoride was added to the cylinder to increase the total pressure to 100 psig. The reactor was heated to 300° C and maintained at that temperature. Periodic samples were taken and analyzed by gas-liquid chromatography. The results are shown, in the area percent, below. For convenience, the high boiling TFCB and OFCB dimer products are not included in the analyses.

Table II

|  | Ethylene | TFE | CF$_2$=CH$_2$ | psig |
|---|---|---|---|---|
| 0 hrs. at 25°C | 3.80 | 4.54 | 91.65 | 90 (at 25° C) |
| 3 hrs. at 300°C | 3.31 | 0.63 | 95.06 |  |
| 8 hrs. at 300°C | 1.30 | 0.00 | 98.70 | 160 (at 300° C) |

The data in the Table II show that the TFE in a mixture including vinylidene fluoride and ethylene can be essentially completely removed by subjecting the mixture of dimerization and/or codimerization. This is accomplished with no significant loss of vinylidene fluoride product and, as earlier noted, a good purity product is obtained.

One skilled in the art in possession of this disclosure having studied the same will recognize that the drawing and the description of the invention are presented in simplified form. Thus, details of equipment design, equipment parts such as vessels, pumps, monitoring devices, etc. have been omitted. These items and related matters can be dealt with by one skilled in the art and do not form any part of the invention here described.

Reasonable variation and modification are possible in the scope of the foregoing disclosure, drawing and the appended claims to the invention the essence of which is that there have been set forth a combination of steps wherewith to remove from vinylidene fluoride produced by cracking tetrafluorocyclobutane, the concomitantly unavoidably produced tetrafluoroethylene without having to deal with tetrafluoroethylene in liquid phase, as described by passing a cracked effluent obtained upon passing tetrafluorocyclobutane through a cracking zone maintained under cracking conditions including elevated temperature into a dimerization zone maintained at a lower temperature effective to cause dimerization, forming OFCB, and/or cyclocodimerization with ethylene, forming TFCB, for a time sufficient to accomplish the desired dimerization or dimerizations and subsequently treating the dimerization effluent as by fractionation to recover desirable vinylidene fluoride substantially freed from tetrafluoroethylene and codimer which is recycled as described.

I claim:

1. A process for producing vinylidene fluoride substantially freed from tetrafluoroethylene which comprises subjecting tetrafluorocyclobutane as can be obtained by the codimerization of tetrafluoroethylene and ethylene to cracking to produce a cracking effluent containing vinylidene fluoride and concomitantly to produce tetrafluoroethylene and ethylene, passing the cracking zone effluent thus obtained into a dimerization zone, therein causing dimerization of the tetrafluoroethylene under codimerization conditions to form at least one of OFCB and TFCB, passing the dimerized effluent to a separation zone, therein separating vinylidene fluoride substantially freed from tetrafluoroethylene.

2. A process according to claim 1 wherein upon separation of the vinylidene fluoride TFCB which has been formed is recycled to the cracking.

3. A process according to claim 1 wherein there is added to the cracking zone effluent an appreciable portion of ethylene to be present in said dimerization zone.

4. A process according to claim 1 wherein the cracking zone effluent is cooled from the temperature at which it is obtained from the cracking zone to a temperature suitable for dimerization in the dimerization zone and is then maintained in said dimerization zone for a time sufficient to accomplish a desired degree of conversion of tetrafluoroethylene.

5. A process according to claim 1 wherein upon separation of the vinylidene fluoride in the separation zone there are obtained at least one of a homodimer and a codimer of tetrafluoroethylene and ethylene and codimer, if present, is recycled to the cracking zone.

6. A process according to claim 1 wherein the cracking is effected thermally at temperatures within the approximate range of from about 500° to about 900° C with a residence time of from about one second up to about 10 minutes and wherein the dimerization is effected at a temperature in the approximate range of from about 300° to about 600° C at a pressure of from about 0 to about 10,000 psig with a residence time of from about 0.1 minute to about 200 hours.

7. A process according to claim 6 wherein there is added to the cracking zone effluent an appreciable portion of ethylene to be present in said dimerization zone.

8. A process according to claim 7 wherein the molar ratio of ethylene to tetrafluoroethylene is in the approximate range of from about 1:1 to about 100:1.

* * * * *